US007427674B2

(12) United States Patent
Aberham et al.

(10) Patent No.: US 7,427,674 B2
(45) Date of Patent: Sep. 23, 2008

(54) SYSTEM AND METHOD FOR DETECTING WEST NILE VIRUS

(75) Inventors: Claudia Aberham, Vienna (AT); Andreas Klotz, Vienna (AT)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 88 days.

(21) Appl. No.: 11/116,791

(22) Filed: Apr. 28, 2005

(65) Prior Publication Data

US 2005/0277114 A1 Dec. 15, 2005

Related U.S. Application Data

(60) Provisional application No. 60/567,105, filed on Apr. 30, 2004.

(51) Int. Cl.
*C12P 19/34* (2006.01)
*C12Q 1/68* (2006.01)

(52) U.S. Cl. .......................... 536/23.1; 435/6; 435/91.2

(58) Field of Classification Search ....................... None
See application file for complete search history.

(56) References Cited

FOREIGN PATENT DOCUMENTS

| | | |
|---|---|---|
| WO | 04/001051 A2 | 12/2003 |
| WO | 2004/076619 A2 | 9/2004 |

OTHER PUBLICATIONS

Boehringer Mannheim 1997 Biocehicals Catalog (1997), 'Non-radioactive labeleing and detection of nucelic acids.' Cover page and p. 95.*
Ahern, H. 'Biochemical, reagent kits offer scientists good return on investment.' The Scientist (1995) 9(15), pp. 20 and 22.*
Savage HM et al 'avian investigations of an epidemic of West Nile fever in Romania in 1996, with serologic and molecular characterization of a virus isolate from mosquitoes.' Am J Trop Med Hyg. Oct. 1999;61(4):600-11.*
Wong K-W et al 'Use of tagged random hexamer amplification (TRHA) to clone and sequence minute quantities of DNA—application to a 180 kb plasmid isolated from Sphingomonas F199.' Nucleic Acids Res. Oct. 1, 1996;24(19):3778-83.*
Lanciotti RA et al 'Origin of the West Nile virus responsible for an outbreak of encephalitis in the northeastern United States.' Science. Dec. 17, 1999;286(5448):2333-7.*
GenBank Locus AF196835, GI:11597239, 'West Nile virus strain NY99-flamingo382-99, complete genome.' 2000, pp. 1-6.*
Buck GA et al 'Design strategies and performance of custom DNA sequencing primers.' Biotechniques. Sep. 1999;27(3):528-36.*
Adb-Elsalam KA 'Bioinformatic tools and guideline for PCR primer design.' African Journal of Biotechnology vol. 2 (5), pp. 91-95, May 2003.*
Anderson JF 'A phylogenetic approach to following West Nile virus in Connecticut.' Proc Natl Acad Sci U S A. Nov. 6, 2001;98(23):12885-9.*
Anderson, J.F., et al.; "A Phylogenetic Approach to Following West Nile Virus in Connecticut"; *Proc of the Natl Acad of Sciences of the USA*; 98(23); pp. 12885-12889 (2001).
Anderson, J.F., et al.; "Isolation of West Nile Virus from Mosquitoes, Crows and a Cooper's Hawk in Connecticut"; *Science*; 286(5448); pp. 2331-2333 (1999).
Briese, T., et al.; "Detection of West Nile Virus Sequences in Cerebrospinal Fluid"; *The Lancet*; vol. 355; pp. 1614-1615 (2000).
Hadfield, T.L., et al.; "Detection of West Nile Virus in Mosquitoes by RT-PCR"; *Molecular and Cellular Probes*; vol. 15; pp. 147-150 (2001).
Lanciotti, R.S., et al.; "Nucleic Acid Sequence-Based Amplification Assays for Rapid Detection of West Nile and St. Louis Encephalitis Viruses"; *Journal of Clinical Microbiol*; vol. 39:12; pp. 4506-4513 (2001).
Lanciotti, R.S., et al.; "Rapid Detection of West Nile Virus from Human Clinical Specimens, Field-Collected Mosquitoes, and Avian Samples by a TaqMan Reverse Transcriptase-PCR Assay"; *Journal of Clinical Microbiology*; vol. 38:11; pp. 4066-4071 (2000).
Porter, K.R., et al.; "Detection of West Nile Virus by the Polymerase Chain Reaction and Analysis of Nucleotide Sequence Variation"; *American Journal of Tropical Medicine and Hygiene*; vol. 48:3; pp. 440-446 (1993).
Shi, P-Y, et al.; "High-Throughput Detection of West Nile Virus RNA"; *Journal of Clinical Microbiology*; vol. 39:4; pp. 1264-1271 (2001).

* cited by examiner

*Primary Examiner*—Jehanne Sitton
*Assistant Examiner*—Stephen Kapushoc
(74) *Attorney, Agent, or Firm*—Townsend and Townsend and Crew LLP

(57) ABSTRACT

The present invention relates to a system for detecting West Nile Virus (WNV) in a sample by detecting nucleic acids having been amplified and comprising the coding region of the membrane protein of WNV. Further, a method and a kit for the detection of amplified nucleic acids comprising the coding region of the membrane protein of WNV are disclosed.

4 Claims, No Drawings

SEQUENCE LISTING

<160> NUMBER OF SEQ ID NOS: 18

<210> SEQ ID NO 1
<211> LENGTH: 25
<212> TYPE: DNA
<213> ORGANISM: West Nile virus

<400> SEQUENCE: 1
aaacagaatc atggatcttg aggaa                                          25

<210> SEQ ID NO 2
<211> LENGTH: 19
<212> TYPE: DNA
<213> ORGANISM: West Nile virus

<400> SEQUENCE: 2
cccaagcatc caaccaatg                                                 19

<210> SEQ ID NO 3
<211> LENGTH: 23
<212> TYPE: DNA
<213> ORGANISM: West Nile virus

<400> SEQUENCE: 3
cctggatatg ccctggtggc agc                                            23

<210> SEQ ID NO 4
<211> LENGTH: 22
<212> TYPE: DNA
<213> ORGANISM: West Nile virus

<400> SEQUENCE: 4
tgatccatgt aagccctcag aa                                             22

<210> SEQ ID NO 5
<211> LENGTH: 20
<212> TYPE: DNA
<213> ORGANISM: West Nile virus

<400> SEQUENCE: 5
tggtctgaca ttgggctttg                                                20

<210> SEQ ID NO 6
<211> LENGTH: 28
<212> TYPE: DNA
<213> ORGANISM: West Nile virus

<400> SEQUENCE: 6
tcggaaggag gacccacat gttgtaac                                        28

<210> SEQ ID NO 7
<211> LENGTH: 24
<212> TYPE: DNA
<213> ORGANISM: West Nile virus -continued

```
<400> SEQUENCE: 7
atattgacac ctgggataga ctag                                               24

<210> SEQ ID NO 8
<211> LENGTH: 17
<212> TYPE: DNA
<213> ORGANISM: West Nile virus

<400> SEQUENCE: 8
cattgtcggc gcactgt                                                       17

<210> SEQ ID NO 9
<211> LENGTH: 25
<212> TYPE: DNA
<213> ORGANISM: West Nile virus

<400> SEQUENCE: 9
atcttctgct ctgcacaacc agcca                                              25

<210> SEQ ID NO 10
<211> LENGTH: 21
<212> TYPE: DNA
<213> ORGANISM: West Nile virus

<400> SEQUENCE: 10
cgggctgtca atatgctaaa a                                                  21

<210> SEQ ID NO 11
<211> LENGTH: 21
<212> TYPE: DNA
<213> ORGANISM: West Nile virus

<400> SEQUENCE: 11
cctcttcagt ccaatcaagg a                                                  21

<210> SEQ ID NO 12
<211> LENGTH: 18
<212> TYPE: DNA
<213> ORGANISM: West Nile virus

<400> SEQUENCE: 12
cggaatgccc cgcgtctt                                                      18

<210> SEQ ID NO 13
<211> LENGTH: 17
<212> TYPE: DNA
<213> ORGANISM: West Nile virus

<400> SEQUENCE: 13
cagaccacgc tacggcg                                                       17

<210> SEQ ID NO 14
<211> LENGTH: 15
<212> TYPE: DNA
<213> ORGANISM: West Nile virus

<400> SEQUENCE: 14
ctagggccgc gtggg                                                         15

<210> SEQ ID NO 15
<211> LENGTH: 24
<212> TYPE: DNA
<213> ORGANISM: West Nile virus
```

-continued

```
<400> SEQUENCE: 15
tctgcggaga gtgcagtctg cgat                                          24

<210> SEQ ID NO 16
<211> LENGTH: 21
<212> TYPE: DNA
<213> ORGANISM: West Nile virus

<400> SEQUENCE: 16
tcagcgatct ctccaccaaa g                                             21

<210> SEQ ID NO 17
<211> LENGTH: 21
<212> TYPE: DNA
<213> ORGANISM: West Nile virus

<400> SEQUENCE: 17
gggtcagcac gtttgtcatt g                                             21

<210> SEQ ID NO 18
<211> LENGTH: 22
<212> TYPE: DNA
<213> ORGANISM: West Nile virus

<400> SEQUENCE: 18
tgcccgacca tgggagaagc tc                                            22
```

SYSTEM AND METHOD FOR DETECTING WEST NILE VIRUS

RELATED APPLICATIONS

This application claims the benefit of priority under 35 U.S.C. § 119 of Provisional Application No. 60/567,105, filed Apr. 30, 2004.

FIELD OF THE INVENTION

The present invention relates to a system for detecting West Nile Virus (WNV) in a sample by detecting nucleic acids having been amplified and comprising the coding region of the membrane protein of WNV. Further, a method and a kit for the detection of amplified nucleic acids comprising the coding region of the membrane protein of WNV are disclosed.

BACKGROUND OF THE INVENTION

West Nile Virus (WNV) has recently emerged as a major US public health concern due to the outbreak of human encephalitis in the USA in 2002 with reported 4165 WNV cases and 284 deaths. Additionally, recent findings of virus transmission by blood transfusion, organ transplantation, and intrauterine infection indicate a need for WNV testing of blood donor specimens. Therefore, the FDA has recommended to screen any blood supply for WNV. Tests which are specific and highly sensitive and which can identify an acute infection with ongoing viremia are in need for such a screening process.

WNV is taxonomically classified within the family Flaviridae, genus *Flavivirus*. For WNV two genetic lineages have been described, lineage 1 having world-wide distribution, ranging from West Africa to the Middle East, Eastern Europe, North America, and Australia. Lineage 2 consists exclusively of strains from Africa which have been isolated only in sub-Saharan Africa and Madagascar.

WNV is arthropod-borne and mainly affects birds in their natural reservoir. Some species, such as the American crow, seem particularly susceptible. Susceptible mammalian species, including horses, dogs, and humans, are incidentally infected through insect bites.

The genome of WNV is a single-stranded plus-sense RNA of approximately 11000 nucleotides. It consists of a 5' non-coding region (NCR, approximately 100 nucleotides), a single open reading frame coding for three viral structural proteins (capsid or core (C), premembrane (prM) and membrane (M), envelope (E)), seven non-structural proteins, and a 3' NCR (approximately 600 nucleotides). The RNA lies within an internal capsid, which is composed of multiple copies of the core protein and is surrounded by an outer, host derived lipid membrane containing the viral envelope and membrane structural proteins which are responsible for many important properties of the virus, including host range, tissue tropism, replication, assembly, and stimulation of B and T cell immune responses. The seven non-structural proteins are involved in viral replication, maturation, and packaging.

WNV is a member of the Japanese encephalitis virus group, which contains Japanese encephalitis (JE), St. Louis encephalitis (SLE), Murray Valley encephalitis (MVE) and Kunjin virus (an Australian subtype of WNV). The close antigenic relationship of the flaviviruses, particular those belonging to the Japanese encephalitis complex, accounts for the serologic cross-reaction observed in the diagnostic laboratory.

WNV diagnostic testing is often based on the detection of immunoglobulin M (IgM) antibodies to WNV. In at least 90% of the infected patients, IgM antibodies against WNV can be detected in sera or cerebral spinal fluid collected on or 8 days after the onset of the disease using an IgM capture Enzyme-Linked Immunosorbent Assay (ELISA). Once developed, IgM antibodies persist for more than 6 months after disease in over 50% of the patients. Due to the persistence of IgM antibodies to WNV, a positive test for IgM is not necessarily a result of an acute infection by WNV. WNV antibodies are known to cross-react with other flaviviruses, which can make the unequivocal identification of WNV difficult. Plaque reduction neutralization assays can be performed to help distinguish among the flaviviruses. Other tests which target the WNV genome and are therefore highly specific are those comprising the enzymatic amplification of nucleic acids. These tests can be used to document minute amounts of virus in blood or tissues of an individuum.

Lanciotti et al. (J. Clin. Microbiol. (2000) 38, 4066-4071) describe the detection of WNV RNA in host organisms by a RT-PCR assay using nucleotide sequences which bind to sequences encoding the core and the pre-membrane proteins of WNV, by a TaqMan assay using nucleotide sequences which bind to the 3' non-coding region of WNV, and by a TaqMan assay using nucleotide sequences which bind to the sequence encoding the envelope protein of WNV. Lanciotti and Kerst (J. Clin. Microbiol. (2001) 39, 4506-4513) describe the detection of WNV RNA by a nucleic acid sequence based amplification (NASBA) assay using nucleotide sequences which bind to sequences encoding the envelope protein of WNV. Shi et al. (J. Clin. Microbiol. (2001) 39, 1264-1271) describe the detection of WNV RNA by a real-time RT-PCR assay using nucleotide sequences which bind to sequences encoding the envelope protein, the non-structural protein 1, and the 3' non-coding region of WNV. Porter et al. (Am. J. Trop. Med. Hyg. (1993) 48, 440-446) describe the detection of WNV RNA by a RT-PCR assay using nucleotide sequences which bind to sequences encoding the non-structural protein 3 of WNV. Briese et al. (Lancet 355 (2000),1614-1615) describe the detection of WNV RNA by a TaqMan assay using nucleotide sequences which bind to sequences encoding the non-structural protein 3 and the non-structural protein 5 of WNV. Hadfield et al. (Mol. Cell Probes 15 (2001), 147-150) describe the detection of WNV RNA by a TaqMan assay using nucleotide sequences which bind to sequences encoding the non-structural protein 3 of WNV.

SUMMARY OF THE INVENTION

It is an object of the present invention to provide a system which allows the detection of nucleic acid sequences containing at least a part of the coding region of the membrane protein of West Nile Virus (WNV) in a sample. In particular, the present invention relates to primer sequences to be used as a set for nucleic acid amplification of a target nucleotide sequence which is at least partially originated from the coding region of the membrane protein of WNV and a probe system directed to the amplified target nucleotide sequence. It is another object of the present invention to provide a method and a kit for detecting nucleic acid sequences containing at least a part of the coding region of the membrane protein of WNV in a sample.

DETAILED DESCRIPTION OF THE INVENTION

One embodiment of the present invention relates to a system for detecting West Nile Virus (WNV) in a sample, containing at least two primer sequences to be used as a set for nucleic acid amplification, which are directed to different target nucleotide sequences, wherein at least one of said target nucleotide sequences or a nucleotide sequence located between said target nucleotide sequences contain at least a part of the coding region of the membrane protein of WNV.

The term "sample" as used herein means any sample containing nucleic acids, preferably RNA. It may be a sample comprising a biological fluid, such as blood or plasma, or tissue of an individuum. The sample may be preferably obtained from a human patient suspected to have an infection with WNV.

The term "primer sequence" as used herein includes any nucleic acid sequence that forms base pairs with a complementary template strand ("target nucleotide sequence") and functions as a starting point for the addition of nucleotides to copy the template strand. The primer sequences of the present invention may be labeled or contain other modifications which allow a detection and/or analysis of amplification products. The primer sequences may also be used for the reverse transcription of WNV RNA into DNA.

The term "target nucleotide sequence" as used herein includes any nucleotide sequence to which one of said primer sequences hybridises under conditions which allow an enzyme having polymerase activity to elongate said primer sequence. Therefore, hybridisation is not limited to the exact complementary sequences of the primer sequences. A lowered binding affinity of the primer, caused e.g. by mismatchs or deletions, can be overcome, e.g. by lowering the annealing temperature.

In a preferred embodiment of the present invention the primer sequences are selected from the group consisting of 5'-AAACAGAATCATGGATCTTGAGG AA-3' (SEQ ID No. 1), 5'-CCCAAGCATCCAACCAATG-3' (SEQ ID No. 2), and nucleotide sequences having 10 to 50 nucleotides and comprising at least a fragment of 10 nucleotides of SEQ ID No. 1 or SEQ ID No. 2.

A further embodiment of the present invention includes a system for detecting WNV in a sample, containing at least two primer sequences as defined above and a probe system comprising at least one nucleotide sequence as a probe which is directed to an amplified target nucleotide sequence prepared by using said primer sequences and originating at least partially from the coding region of the membrane protein of WNV.

The term "probe" as used herein means any nucleotide sequence that is used to detect amplified target nucleotide sequences by hybridisation.

In a preferred embodiment of the present invention the probe is selected from the group consisting of 5'-CCTG-GATATGCCCTGGTGGCAGC-3' (SEQ ID No. 3) or nucleotide sequences having 10 to 50 nucleotides and comprising at least a fragment of 10 nucleotides of SEQ ID No. 3.

According to the present invention the probe may be linked, preferably covalently linked to at least one detectable label. The term "detectable label" does not exhibit any particular limitation and may be selected from the group consisting of radioactive labels, fluorescent dyes, compounds having an enzymatic activity, magnetic labels, antigens, and compounds having a high binding affinity for a detectable label. For example, a radioactively or fluorescently labeled probe can be used to detect a part of the coding region of the membrane protein of WNV, e.g. after electrophoresis. Fluorescent dyes linked to a probe may serve as a detection label, e.g. in a real-time PCR. A compound having an enzymatic reactivity such as the enzyme luciferase which produces a light signal upon contact with the respective substrate can also be used as a detectable label which may be linked covalently to said probe. Labeling the probe of the present invention with magnetic beads allows a selective extraction of nucleic acids containing a fragment of the coding region of the membrane protein of WNV from samples. Coupling a probe to an antigen allows the detection of the probe by an antibody/enzyme-complex (the enzyme being e.g. phosphatase) catalysing a detectable color reaction when using a suitable substrate. A compound with a high binding affinity for a different detectable label such as biotin which binds to a detectable label covalently linked to e.g. streptavidine, is a further possibility for making a probe of the present invention detectable.

When fluorescent dyes are used as a detection label linked to the probe in a real-time PCR the probe system of the present invention may be any kind of probe system known in the art for the detection of amplification products in a real-time PCR, such as TaqMan probes, Molecular Beacons, Scorpion probes, as well as Light Cycler probes or other Fluorescent Resonance Energy Transfer (FRET) based probes. TaqMan probes contain a reporter at one end and a quencher which prevents the reporter from emitting a detectable fluorescent signal at the other end. After hybridisation of the probe with a complementary nucleotide sequence the 5'→3' exonuclease activity of the polymerase cleaves the probe so that the quencher is no longer close to the reporter and a detectable fluorescent signal is emitted. Molecular Beacons are also labeled with a reporter at one end and a quencher which prevents the reporter from emitting a detectable fluorescent signal at the other end. A self-complementary sequence at both ends of the probe gives rise to a hairpin structure of the probe. This hairpin structure is resolved as soon as the probe hybridises with a complementary nucleotide sequence. This resolving of the hairpin structure leads to a distance between quencher and reporter which is sufficient for a detectable fluorescent light emission by the reporter. Scorpion probes uni-probes consist of a bilabelled fluorescence probe held in a hairpin conformation. It contains a reporter dye at the 5'end and an internal quencher dye. The quencher is linked to the 5'end of the specific primer. Close distance results in a quenching of the reporter signal. During the cycle the hairpin unfolds caused by the hybridisation of the probe's 5'end and the new synthesised target sequence. Then the reporter dye is not close to the quencher any more and the fluorescence can be detected by a real-time PCR instrument. The Light Cycler probe system consists of two probes which are directed against adjacent target nucleotide sequences and which are labeled with different fluorescent dyes. After hybridisation the fluorescent dye linked to one probe is excited and subsequently induces the emission of a detectable fluorescent signal by the fluorescent dye linked to the other probe.

The above-defined primer and probe sequences may be used without a label as well as labeled with any commercially available dye alone or in any mixture thereof. Examples of fluorescent dyes are TAMRA, NED, PET, ROX, LIZ, FAM, VIC, HEX, JOE, TET, ROX, Cy3, Cy5, Red705, Red640, Texas Red, Biotin Digoxygenin, Rhodamine, Fluorescein, phosphate thiol. The above-defined primer and probe sequences may be used in a conventional RT-PCR, a Transcription-Mediated Amplification (TMA) assay, a bDNA assay, or a real-time RT-PCR assay with or without labels linked thereto or in a SNP analysis. With the RNA or the RT-PCR product further investigations like RFLP, SSCP, Southern or Northern Blot (e.g. using the described oligonucleotides as a hybridisation probe), or ELISA may be carried out.

The nucleotide sequences described here are given as DNA sequences. However, corresponding RNA sequences or nucleotide sequences having any modifications which do not negatively affect the intended function are also encompassed by the present invention.

The system of the present invention can be used for the detection of WNV lineages, such as known lineage 1 and WNV lineage 2, and preferably WNV lineage 1.

A further object of the invention relates to a method for detecting WNV RNA in a sample, comprising the steps of
(a) amplifying a specific nucleotide sequence of said WNV RNA using at least two primer sequences which are directed to different target nucleotide sequences, wherein at least one of said target nucleotide sequences or a nucleotide sequence located between said target nucleotide sequences contain at least a part of the coding region of the membrane protein of WNV, and
(b) detecting the amplification products resulting from said amplification process.

In a preferred embodiment the sample comprises body fluids or tissues of vertebrates, such as mammals, including human beings, or birds, and of invertebrates like arthropods, including whole insect samples.

The term "amplification" as used herein means an enzymatically catalysed amplification of a particular nucleotide sequence by an enzyme having a polymerase activity. Examples of the enzyme are Taq polymerase, Pfu polymerase, or rTth polymerase. The amplification may be carried out in a PCR.

In a preferred embodiment of the present invention the RNA may be transcribed into DNA using an enzyme having a reverse transcription activity, i.e. the ability to catalyse the synthesis of a cDNA nucleotide sequence complementary to a RNA nucleotide sequence, prior to amplification.

There is no particular limitation to the reagents or conditions used for a reverse transcription or an amplification carried out according to the present invention, and any system known in the art or commercially available can be employed.

Detection of amplification products may be carried out by any method known in the art for the detection of nucleic acids, e.g. by hybridising with probe sequences, by the use of radioactively or chemically labeled primer sequences, or by the use of a DNA-intercalating fluorescent dye, like SYBR Green or ethidium bromide. Detection of the amplification products using a DNA-intercalating fluorescent dye may be carried out by detecting the amplification products during the amplification reaction or after the amplification reaction, e.g. by analysis of the melting curve of the double-stranded amplification products or by staining the amplification products after electrophoresis. In a preferred embodiment of the present invention at least one nucleotide sequence is used as a probe for detecting the amplification products.

In a preferred embodiment of the present invention the amplification reaction and the detection of the amplification products may be carried out in a real-time PCR assay carried out in any commercially available thermocycler having a system for the detection of a fluorescent signal.

In a preferred embodiment the above-defined method is a method for the detection of WNV using real-time RT-PCR.

A further object of the present application is to provide a kit for detecting West Nile Virus (WNV) in a sample, containing at least two primer sequences which are directed to different target nucleotide sequences, wherein at least one of said target nucleotide sequences or the nucleotide sequence located between said target nucleotide sequences contain at least a part of the coding region of the membrane protein of WNV. The kit may be used for the diagnosis of an infection with WNV, including lineage 1 and 2, in a host organism such as mammals, e.g. humans. In a preferred embodiment the kit further contains a probe system as defined above. In a further preferred embodiment of the invention the kit comprises a system for the detection of WNV lineage 1.

The present invention will be further illustrated in the following examples, without any limitation thereto.

EXAMPLES

Example 1

Optimization of Reaction Conditions of the Real-time RT-PCR Assay (A) Primer Sequences and Probes to be Tested:

The following primer and probes directed to target nucleotide sequences located in different regions of the WNV genome are tested under the same reaction conditions. As a control two primer/probe sets (WN3'NC and ENV) are selected which are already published in the prior art and are tested under standard reaction conditions. The nucleotide positions of the respective primer/probe are indicated in brackets and refer to WNV isolate NY99 (Genbank Acc. No. AF196835). In the assay the respective probes carry the 5' label 6-FAM and the 3' label TAMRA.

```
Membrane Protein:
MPMF1 (forward):
5'-AAACAGAATCATGGATCTTGAGGAA-3'         (833-857)
                                        (SEQ ID No. 1)

MPMR1 (reverse):
5'-CCCAAGCATCCAACCAATG-3'               (903-885)
                                        (SEQ ID No. 2)

MPMP1 (probe):
5'-CCTGGATATGCCCTGGTGGCAGC-3'           (859-881)
                                        (SEQ ID No. 3)

3'non coding region:
3-UTRF1 (forward):
5'-TGATCCATGTAAGCCCTCAGAA-3'            (10598-10619)
                                        (SEQ ID NO. 4)

3-UTRR1 (reverse):
5'-TGGTCTGACATTGGGCTTTG-3'              (10674-10655)
                                        (SEQ ID NO. 5)

3-UTRP1 (probe):
5'-TCGGAAGGAGGACCCCACATGTTGTAAC-3'      (10625-10652)
                                        (SEQ ID NO 6)

3'UTRF2 (forward):
5'-ATATTGACACCTGGGATAGACTAG-3'          (10926-10949)
                                        (SEQ ID NO 7)

3'UTRR2 (reverse):
5'-CATTGTCGGCGCACTGT-3'                 (11000-10984)
                                        (SEQ ID NO 8)

3'UTRP2 (probe):
5'-ATCTTCTGCTCTGCACAACCAGCCA-3'         (10953-10977)
                                        (SEQ ID NO 9)

Nucleocapsid ("core protein C"):
CPF1 (forward):
5'-CGGGCTGTCAATATGCTAAAA-3'             (130-150)
                                        (SEQ ID NO 10)

CPR1 (reverse):
5'-CCTCTTCAGTCCAATCAAGGA-3'             (192-172)
                                        (SEQ ID NO 11)
```

-continued

CPP1 (probe):
5'-CGGAATGCCCCGCGTCTT-3' (153-170)
(SEQ ID NO 12)

3' non Coding Region:

(taken from reference: Lanciotti et al., Rapid Detection of West Nile Virus from Human Clinical Specimens, Field-Collected Mosquitoes, and Avian Samples by a TaqMan Reverse Transcriptase PCR Assay, Journal of Clinical Microbiology (2000) 38, 4066-4071)

WN3'NC-forward:
5'-CAGACCACGCTACGGCG-3' (10668-10684)
(SEQ ID NO 13)

WN3'NC-reverse:
5'-CTAGGGCCGCGTGGG-3' (10770-10756)
(SEQ ID NO 14)

WN3'NC-probe:
5'-TCTGCGGAGAGTGCAGTCTGCGAT-3' (10691-10714)
(SEQ ID NO 15)

Envelope:

(taken from reference: Lanciotti et al., Rapid Detection of West Nile Virus from Human Clinical Specimens, Field-Collected Mosquitoes, and Avian Samples by a TaqMan Reverse Transcriptase PCR Assay, Journal of Clinical Microbiology (2000) 38, 4066-4071)

ENVF1: 5'-TCAGCGATCTCTCCACCAAAG-3' (1160-1180)
(SEQ ID NO 16)

ENVR1: 5'-GGGTCAGCACGTTTGTCATTG-3' (1229-1209)
(SEQ ID NO 17)

ENVP1: 5'-TGCCCGACCATGGGAGAAGCTC-3' (1186-1207)
(SEQ ID NO 18)

(B) Testing of Different Temperatures for the Reverse Transcription:

During the reverse transcription temperatures of 48° C., 55° C., 60° C. are tested. Primer/probe sets for UTR1, MPM and WN3'NC are tested.

Result: Lower reverse transcription temperatures lead to unspecific signals during the reaction. The ideal temperature is 60° C. for the reverse transcription, which is according to the recommended temperature of the supplier of the kit (Protocol "TaqMan EZ RT-PCR Kit", Applied Biosystems, Part No. 402877 Rev. C, 04/2002).

(C) Testing of Different Annealing Temperatures:

A range of annealing temperatures (56° C., 58° C., 60° C., 62° C., 64° C.) is tested to identify the ideal annealing temperature. The tests are performed by analyzing the deltaRn-value after the last cycle (cycle 45) of the real-time RT-PCR and by comparing the deltaRn-values of the different annealing temperatures. The following primer/probe sets are tested at the given temperatures: UTR1, UTR2, MPM, and WN3'NC.

Result: With the primer/probe sets UTR1 and UTR2 only very low signals are generated. For the primer/probe sets WN3'NC and MPM sufficient signals are achieved. Using the WN3'NC set the ideal annealing temperature is 60° C. and using the MPM set the ideal annealing temperature is 60° C.

(D) Testing of Different Primer Concentrations:

A primer matrix is tested to identify the ideal concentration of the forward and the reverse primer. Following concentrations in all possible combinations are tested: 50 nM, 300 nM, 900 nM final concentration. Both, MPM and WN3'NC primer/probe sets, are tested in four replicates. In all tests the amount of probe per reaction is constant. The tests of different primer concentrations are performed by analyzing the deltaRn-value after the last cycle (cycle 45) and the Ct-value of the real-time RT-PCR. The results of the different primer concentrations are compared.

Result: For both primer/probe sets (MPM and WN3'NC) the ideal concentration of the primers is 300 nM for the forward primer and 900 nM for the reverse primer resulting in a maximum in the delta-Rn-value and a minimum in the Ct-value.

(E) Testing of Different Probe Concentrations:

In a next step the primer concentration of the reaction is kept constant and the concentration of the probe is varied in order to identify the ideal concentration. Following final concentrations of the MPM and WN3'NC probe are tested: 10 nM, 20 nM, 50 nM, 100 nM, 150 nM, 200 nM, 250 nM, 300 nM, 350 nM, 400 nM, 500 nM, 700 nM, 1000 nM. In all tests the primer concentrations are kept constant with the ideal combination determined in the primer matrix tested previously (300/900 nM). The tests of different probe concentrations are performed by analyzing the deltaRn-value after the last cycle (cycle 45) and the Ct-value of the real-time RT-PCR. The results of the different probe concentrations are compared.

Result: For both primer/probe sets (MPM and WN3'NC) the ideal concentration of the probes is 300 nM resulting in a maximum of the deltaRn-value, a minimum of the Ct-value, and a minimum of unwanted background signals.

(F) Testing of Different Manganese Acetate Concentrations:

Manganese acetate (MnAc2) concentrations of 1 mM, 1.5 mM, 2 mM, 2.5 mM, 3 mM, 3.5 mM, 4 mM, 4.5 mM are tested. The tests of different $MnAc_2$ concentrations are performed by analyzing the deltaRn-value after the last cycle (cycle 45) and the Ct-value of the real-time RT-PCR. The results of the different $MnAc_2$ concentrations are compared.

Result: For both primer/probe sets (MPM and WN3'NC) the ideal concentration of $MnAc_2$ is 3.5 mM resulting in a maximum of the deltaRn-value and a minimum of the Ct-value.

The tests A-F show that the nucleotide sequences located in the MPM region of the WNV genome display the highest sensitivity. The ideal reaction conditions resulting of the above tests are chosen for the MPM primer/probe and all subsequent tests are carried out with optimized reaction conditions.

Example 2

Testing of External Controls

WNV Preparations Provided by BBI Diagnostics (WNV Lineage 1, Strain: NY99-Flamingo 382-99):

Currently three different WNV preparations are available as controls. They are provided by BBI Diagnostics (West Bridgewater, Mass., USA) and are suggested to be used as WNV qualification panels. Quantitative amounts indicated by BBI (see: Ji J., Chen X. and Manak M. "TaqMan Probe Assay for the Detection of West Nile Virus", 16th Annual San Diego Conference 2001) were determined by a TaqMan based RT-PCR assay using probes specific for WNV.

WNV RNA Panel QWN701 consists of 12 positive and 3 negative samples. The WNV stock, lineage 2 (Uganda), was isolated from an infected individual and amplified in a cell culture. The amount of target RNA copies/ml ranges from 30 to 10000.

WNV RNA Panel QWN702 consists of 12 positive and 3 negative samples as well. The WNV stock lineage 1 (NY Isolate 99) was amplified in a cell culture. The amount of target RNA copies/ml ranges from 30 to 10000.

WNV RNA Panel QWN701 and QWN702 are tested using the MPM primers and probe. The MPM primers and probe detect 100 copies/ml of lineage 1 in all of the performed tests.

WNV RNA Positive Control and Negative Control provided by BBI Diagnostics (Positive Control: "ACCURON 365", Negative Control: "ACCURON 865") are used as an extraction control during testing. As specified by the supplier the Positive Control has a mean value of 300 copies/ml and the Negative Control is negative for WNV RNA. The controls are included on regular basis in test runs. Thereby, the positive controls are detected successfully and the negative controls do not show any signal in all tests carried out. The reproducibility of the MPM-assay is determined by 12 independent tests with the control (Table 1):

TABLE 1

Reproducibility of the MPM-Assay

| mean value (Ct) | standard deviation | CV % |
| --- | --- | --- |
| 33.57 | 0.78 | 2.31% |

As described below in Example 5, the routine testing for WNV is performed with 10 µl extract of human plasma. Under those conditions the WNV RNA Panel QWN702 with 1000 copies/ml, 300 copies/ml, 100 copies/ml, 30 copies/ml and 0 copies/ml was carried out with the primer pairs and probes MPM and WN3'NC. The sample with the concentration of 30 copies/ml was detected successfully only with the MPM primer pair and probe.

According to data from BBI Biotech and Chiron which was shown in presentations at the Sogat Meeting dated Jul. 3, 2003 in Langen, Germany, the detection limit of the MPM system is better or similar compared to that of other described systems.

Example 3

Specificity of the MPM Primer and Probe (A) Control Run:

A control run using low amounts of Hepatitis A Virus, Hepatitis B Virus, Hepatitis C Virus, Human Immunodeficiency Virus and Parvovirus B19 is subjected to the RT-PCR assay for WNV RNA using the MPM primer/probe system. No signal for WNV is detectable, which is an indication for the specificity of the chosen MPM primer/probe-system.

(B) Database Search Using BLAST:

A BLAST (Basic Local Alignment Search Tool, provided by the National Center for Biotechnology Information (USA)) search of the MPM nucleotide sequences MPMF1, MPMR1, and MPMP1 results in hits with reasonable homology exclusively within WNV sequences. Only for MPMR1 a homology with Z71980 (*malus domestica*—apple tree) was found. Thus, it can be assumed that the MPM primer and probe system has a sufficient specificity.

Example 4

Construction of an Internal Control Using the Sequence Coding for the Membrane Protein of WNV A long fragment within the coding sequence of the membrane protein M of WNV containing the binding sites for the MPM primer and probe is amplified by RT-PCR. This fragment is cloned into a vector and used as a template for a mutagenesis following a standard protocol. Thereby, a new mutagenized sequence is generated at the binding site of the probe which can be detected with a new probe (different from the probe for the WNV wild type-sequence) as an internal control.

Example 5

Possible Set-up of an Assay as a Kit

Protocol of the RNA Extraction:

For the extraction of the nucleic acid a sample volume of 1 ml plasma is used. The nucleic acid is isolated by standard procedures. The purified nucleic acid is obtained in a final volume of 60 µl of water.

Protocol of the Amplification and Detection:

10 µl of the RNA extracted as described above are used for the real-time RT-PCR. In a preferred embodiment runs can be performed on a TaqMan (Applied Biosystems) using the ABI Prism 7700 Sequence Detection System and the ABI Prism 7900HT Sequence Detection System.

Principle of the Technique:

A short fragment of the viral nucleic acid is amplified in a PCR using primer and a temperature stable DNA polymerase. The concurrent cleavage of a probe specifically binding in between the two primer sites (5' nuclease assay) results in the release of the fluorescent dye linked to the probe. The increase in the fluorescent intensity, which is directly proportional to the amount of amplifications products, is measured.

Mastermix:

A 50 µl reaction volume consisting of 30 µl mastermix, 10 µl water, and 10 µl extracted RNA is used for the real-time RT-PCR. In Table 2 a preferred embodiment of a reaction mix serving as a mastermix is described:

TABLE 2

Mastermix

| reaction mix for 1 sample | [µl] |
| --- | --- |
| H$_2$O | 2.2 |
| 5 × EZ-buffer | 10.0 |
| MnAc$_2$ (25 mM) | 7.0 |
| dNTP's (10 mM each) | 6.0 |
| MPMF1 (40 µM) (SEQ ID No. 1) | 0.4 |
| MPMR1 (40 µM) (SEQ ID No. 2) | 1.1 |
| MPMP1 (20 µM) (SEQ ID No. 3) | 0.8 |
| AmpErase UNG (1 U/µl) | 0.5 |
| rTth (2.5 U/µl) | 2.0 |

In this test the primers are unlabeled, the probe is labelled at the 3'end with TAMRA and at the 5'end with FAM.

Temperature Program for the Real-Time RT-PCR:

2 min 50° C.;

20 min 60° C.;

5 min 95° C.; and 20 sec 94° C./1 min 60° (45 cycles).

Data Analysis:

In a preferred embodiment the real-time RT-PCR is performed on a TaqMan (Applied Biosystems) and the analysis is carried our with the Sequence Detection Software SDS2.0. An internal Standard Operation Procedure is used for the analysis.

We claim:

1. A system for detecting West Nile Virus (WNV) in a sample, said system comprising a first and a second primer and a probe, wherein the sequence of the first primer consists of 5'-AAACAGAATCATGGATCTTGAGGAA-3' (SEQ ID NO:1), the sequence of the second primer consists of 5'-CCCAAGCATCCAACCAATG-3' (SEQ ID NO:2), and the sequence of the probe consists of 5'-CCTGGATATGC-CCTGGTGGCAGC-3' (SEQ ID NO:3).

2. The system of claim 1, wherein the probe is covalently linked to at least one detectable label.

3. The system of claim 2, wherein said detectable label is selected from the group consisting of radioactive labels, fluorescent dyes, compounds having an enzymatic activity, magnetic labels, antigens, and compounds having a high binding affinity for a detectable label.

4. A kit for detecting West Nile Virus (WNV) in a sample, said kit comprising a first and a second primer and a probe, wherein the sequence of the first primer consists of 5'-AAA-CAGAATCATGGATCTTGAGGAA-3' (SEQ ID NO:1), the sequence of the second primer consists of 5'-CCCAAG-CATCCAACCAATG-3' (SEQ ID NO:2), and the sequence of the probe consists of 5'-CCTGGATATGCCCTGGTG-GCAGC-3' (SEQ ID NO:3).

* * * * *